US00PP17513P2

(12) United States Plant Patent
Mehring-Lemper

(10) Patent No.: US PP17,513 P2
(45) Date of Patent: Mar. 20, 2007

(54) ***MONARDA* PLANT NAMED 'MONDID 0803'**

(50) Latin Name: ***Monarda didyma* L.**
Varietal Denomination: Mondid 0803

(75) Inventor: Manfred Mehring-Lemper, Hann. Münden (DE)

(73) Assignee: Ernst Benary Samenzucht GmbH, Münden ( * ) Notice: Subject to any disclaimer, the term of this patent is extended or adjusted under 35 U.S.C. 154(b) by 21 days.

(21) Appl. No.: 11/251,145

(22) Filed: Oct. 14, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—The Webb Law Firm

(57) ABSTRACT

A new and distinct cultivar of *Monarda* plant named 'Mondid 0803', characterized by its vibrant reddish-purple colored flowers and its powdery mildew resistance.

3 Drawing Sheets

Botanical classification: *Monarda didyma* L.
Varietal denomination: 'Mondid 0803'.

BACKGROUND OF THE INVENTION

The present invention comprises a new and distinct cultivar of *Monarda didyma* L. known by the varietal name 'Mondid 0803'. The new variety is a product of a planned breeding program conducted in Germany. The purpose of the breeding program was to develop new powdery mildew resistant cultivars. The new variety was selected as a single plant growing among seedlings from a cross between two unnamed and unpatented *Monarda didyma* L. plants. The new variety is similar to its parents in habit and flower type, but exhibits powdery mildew resistant. The mildew resistance trait distinguishes 'Mondid 0803' as a new and distinct cultivar from others known to the breeder. Asexual reproduction of the new cultivar in Germany by side shoot cuttings has shown that the unique features of the new variety are stable and reproduced true to type in successive propagations by asexual reproduction.

BRIEF DESCRIPTION OF THE DRAWINGS

The accompanying colored photographic drawings illustrate the new variety, with the colors being as nearly true as is possible to obtain in colored illustrations of this type.

DESCRIPTION OF THE PLANT

Figure 1:
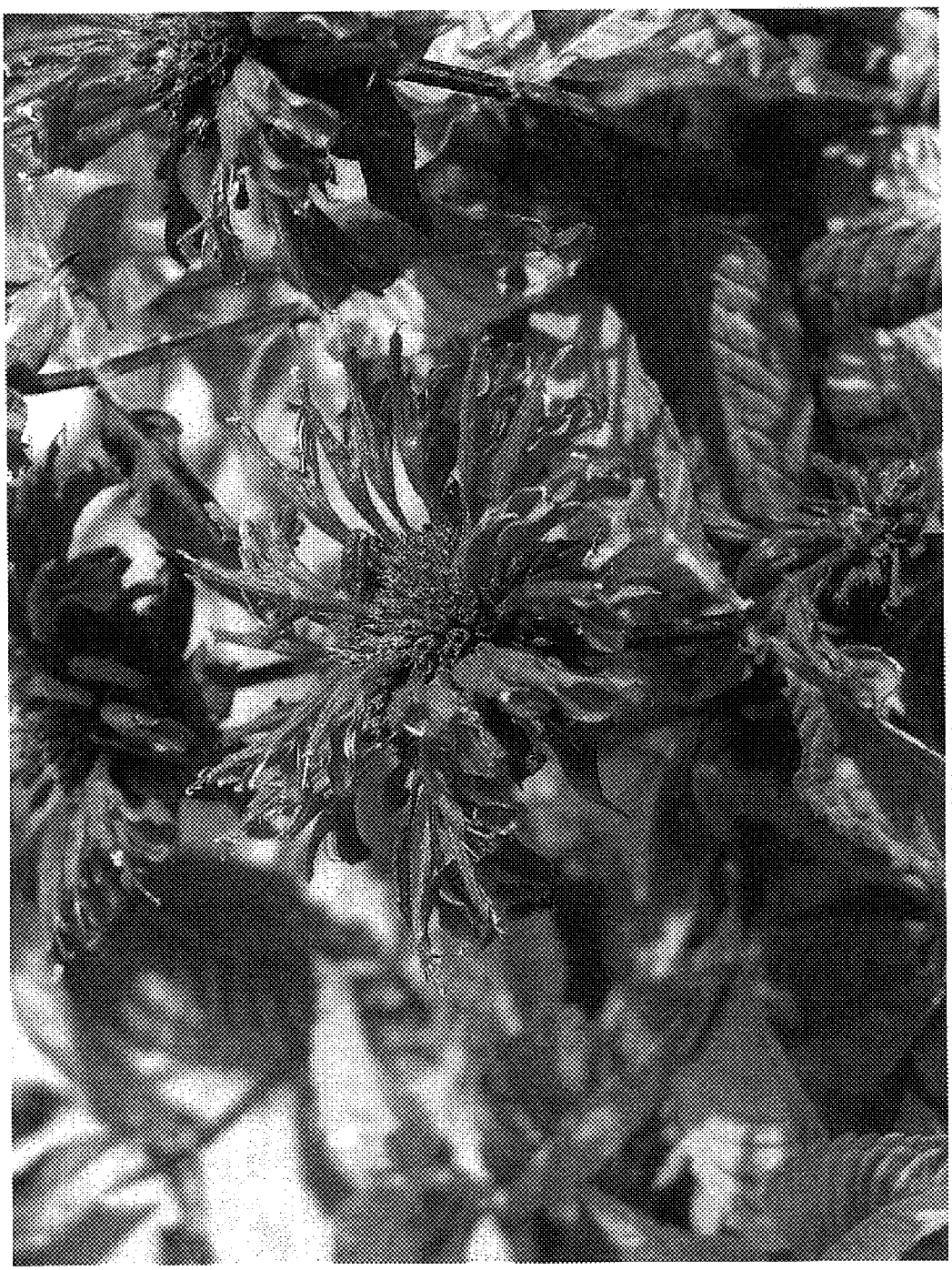
FIG. 1 is a close-up of the blooms of the new variety.
Figure 2:
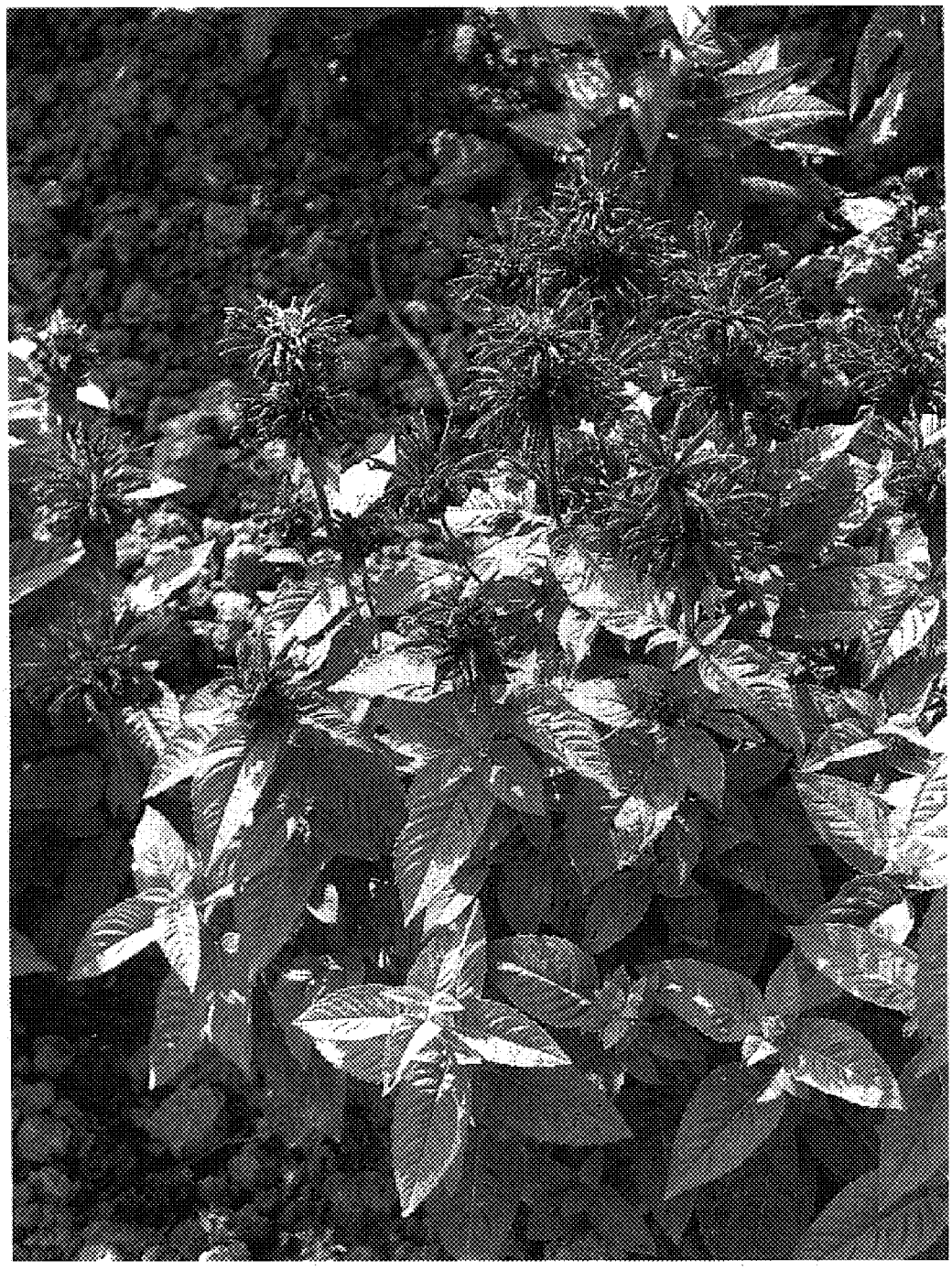
FIG. 2 illustrates an entire plant of the new variety.
Figure 3:
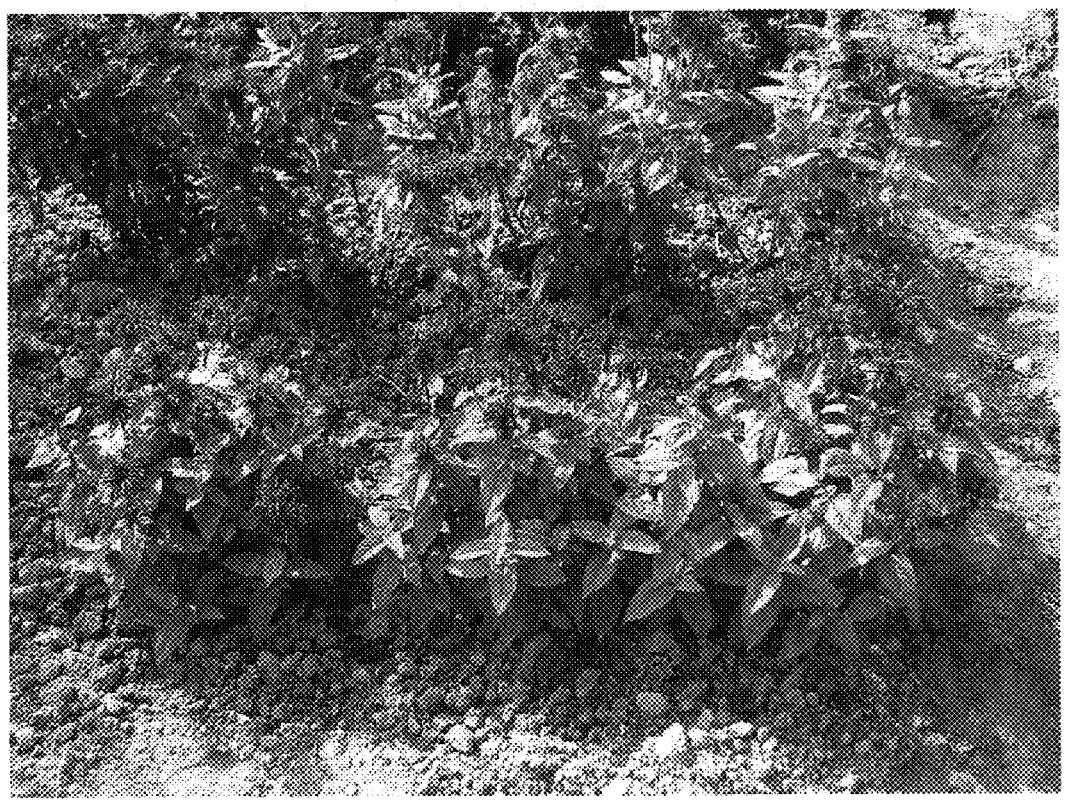
FIG. 3 shows multiple entire plants of the new variety.

The cultivar 'Mondid 0803' has not been observed under all possible environmental conditions. The phenotype may vary somewhat with variations in environment such as temperature, day length and light intensity.

However, there is no variance in genotype.

In the following description, color references are made to The Royal Horticultural Society Colour Chart, except where general terms of ordinary dictionary significance are used. Plants were grown outdoors in a field. The plant was 18 months old when described under natural outdoor light conditions on a sunny day.

PLANT

Form: Mounded.
Height from soil to top of flowers: 16" (~40 cm.) under dry conditions.
Plant diameter: 16" (~40 cm.).
Vigor: Medium.
Branching habit: Good basal and shoot branching.
Lateral branches:
- *Form.*—Upright.
- *Color.*—Green Group 137B.
- *Length.*—10"–15" (~25–38 cm.).
- *Diameter.*—Up to 7" (~18 cm.).
- *Internode length.*—2" (~5 cm.).
- *Strength.*—Strong.
- *Quantity.*—Multiple.

Foliage:
- *Arrangement.*—Alternate.
- *Number of leaves per stem.*—Approximately six or more leaf pairs.
- *Size of leaf.*—Length: 3"–4" (~8–10 cm.). Width: 1"–2" (~3–5 cm.).
- *Shape of leaf (generally).*—Pointed, oviform.
- *Shape of apex.*—Pointed.
- *Margin type.*—Dentate.
- *Fragrance.*—Light mint.
- *Color.*—Young leaves: Upper surface: Green Group 137B. Lower surface: Green Group 137C. Mature leaves: Upper surface: Yellow-Green Group 147A. Lower surface: Green Group 137B.
- *Petiole.*—Length: 0.6" (~1.5 cm.). Diameter: 0.01" (~0.02 cm.). Color: 146D turning slightly purple at base. Strength: Strong.
- *Veins.*—Venation pattern: One central vein. Color: Upper surface: The central vein is 146D turning slightly purple. Lower surface: Pale green, 146D.

FLOWER

Natural flowering season at specified location(s): Germany, Hardiness Zones VII–VIII.

Flower type and habit: Typical labiate flower.
Number of flowers per plant: Numerous inflorescences.
Fragrance: Mint.
Longevity: Single flowers last a few days, inflorescences can last up to 2–3 weeks.
Verticillaster height: 2" (~5 cm.).
Verticillaster diameter: 3" (~8 cm.).
Flower height: length 1" (~3 cm.).
Flower diameter: 1"–2.4" (~3–6 cm.).
Bud:
*Stage of development when described.*—At the showing of first color.
*Shape.*—Round; tubular.
*Diameter.*—0.01" (~0.02 cm.).
*Length.*—0.01" (~0.03 cm.).
Corolla:
*Arrangement.*—Typically labiate.
*Length.*—Upper lip: 0.015" (~0.04 cm.). Lower lip: 0.04" (~0.10 cm.).
*Width.*—Upper lip: 0.006" (~0.015 cm.). Lower lip: 0.024" (~0.06 cm.).
*Shape.*—Upper lip: Tubular. Lower lip: Spoon-shaped, curled upwards.
*Apex.*—Upper lip: Round.
*Base.*—Upper lip: Tubular. Lower lip: Tubular.
*Color.*—When opening: Upper lip (upper and lower surfaces): Red-Purple Group 60A. Lower lip (upper and lower surfaces): Red-Purple Group 63A. Fully opened: Upper lip (upper and lower surfaces): Red-Purple Group 60A. Lower lip (upper and lower surfaces): Red-Purple Group 63A.
Calyx: Color (when opening): Red-Purple Group 59A. Color (fully opened): Red-Purple Group 59A.
Disease resistance: Resistant to powdery mildew.

REPRODUCTIVE ORGANS

Stamens:
*Number* (*per flower*).2.
*Filament length.*—0.06" (~0.14 cm.).
*Anthers.*—Shape: Linear. Length: 0.008"–0.01" (~0.02–0.03 cm.). Color: Reddish purple.
*Pollen.*—Color: White.
Pistils:
*Length.*—0.06" (~0.14 cm.).
*Style color.*—Purple.
*Stigma shape.*—Needle-like with two lobes.

I claim:

1. A new and distinct variety of *Monarda* plant named 'Mondid 0803' as herein described and illustrated.

* * * * *